US010064603B2

(12) United States Patent
Lee

(10) Patent No.: US 10,064,603 B2
(45) Date of Patent: Sep. 4, 2018

(54) ULTRASOUND DIAGNOSIS APPARATUS, METHOD OF CONTROLLING ULTRASOUND DIAGNOSIS APPARATUS, AND STORAGE MEDIUM HAVING THE METHOD RECORDED THEREON

(71) Applicant: SAMSUNG MEDISON CO., LTD., Hongcheon-gun (KR)

(72) Inventor: Seung-ju Lee, Hongcheon-gun (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 338 days.

(21) Appl. No.: 14/751,997

(22) Filed: Jun. 26, 2015

(65) Prior Publication Data

US 2016/0000410 A1     Jan. 7, 2016

Related U.S. Application Data

(60) Provisional application No. 62/020,645, filed on Jul. 3, 2014.

(30) Foreign Application Priority Data

Oct. 27, 2014  (KR) .................. 10-2014-0146427

(51) Int. Cl.
*G06F 3/048* (2013.01)
*A61B 8/00* (2006.01)
*G06F 3/0488* (2013.01)

(52) U.S. Cl.
CPC .............. *A61B 8/54* (2013.01); *A61B 8/4263* (2013.01); *A61B 8/463* (2013.01); *A61B 8/465* (2013.01);
(Continued)

(58) Field of Classification Search
CPC ....................................................... G06F 3/048
See application file for complete search history.

(56) References Cited

U.S. PATENT DOCUMENTS

2004/0242988 A1    12/2004   Niwa et al.
2010/0180219 A1     7/2010   Sung et al.
(Continued)

FOREIGN PATENT DOCUMENTS

JP           5265619 A      10/1993
JP        2003284711 A      10/2003
(Continued)

OTHER PUBLICATIONS

Communication dated May 31, 2016 issued by Korean Intellectual Property Office in counterpart Korean Application No. 10-2014-0146427.

(Continued)

*Primary Examiner* — Peiyong Weng
(74) *Attorney, Agent, or Firm* — Sughrue Mion, PLLC

(57) ABSTRACT

An ultrasound diagnosis apparatus is provided, including a touch display which displays a graphical user interface (GUI) including a plurality of input buttons and receives an input of a user; and a controller which detects an input posture of the user and sets a display mode of the GUI based on the detected input posture. The GUI has a first display mode and a second display mode, and the first display mode and the second display mode are modes in which locations of at least one of the plurality of input buttons included in the GUI are differently displayed.

28 Claims, 16 Drawing Sheets

(52) U.S. Cl.
CPC .......... *A61B 8/467* (2013.01); *G06F 3/04886* (2013.01); *A61B 8/4405* (2013.01)

(56) References Cited

U.S. PATENT DOCUMENTS

| | | | |
|---|---|---|---|
| 2012/0172726 A1* | 7/2012 | Sakai | A61B 8/00 600/443 |
| 2012/0196258 A1 | 8/2012 | Geijsen et al. | |
| 2013/0237288 A1* | 9/2013 | Lee | G06F 3/041 455/566 |
| 2014/0005550 A1* | 1/2014 | Lu | A61B 8/465 600/459 |
| 2015/0301712 A1 | 10/2015 | Ban et al. | |

FOREIGN PATENT DOCUMENTS

| | | |
|---|---|---|
| JP | 2009142476 A | 7/2009 |
| KR | 10-2010-0084037 A | 7/2010 |
| KR | 101031494 B1 | 4/2011 |
| KR | 10-2015-0003560 A | 1/2015 |

OTHER PUBLICATIONS

Communication dated Nov. 27, 2015 by the Korean Intellectual Patent Office in related Application No. 10-2014-0146427.

\* cited by examiner

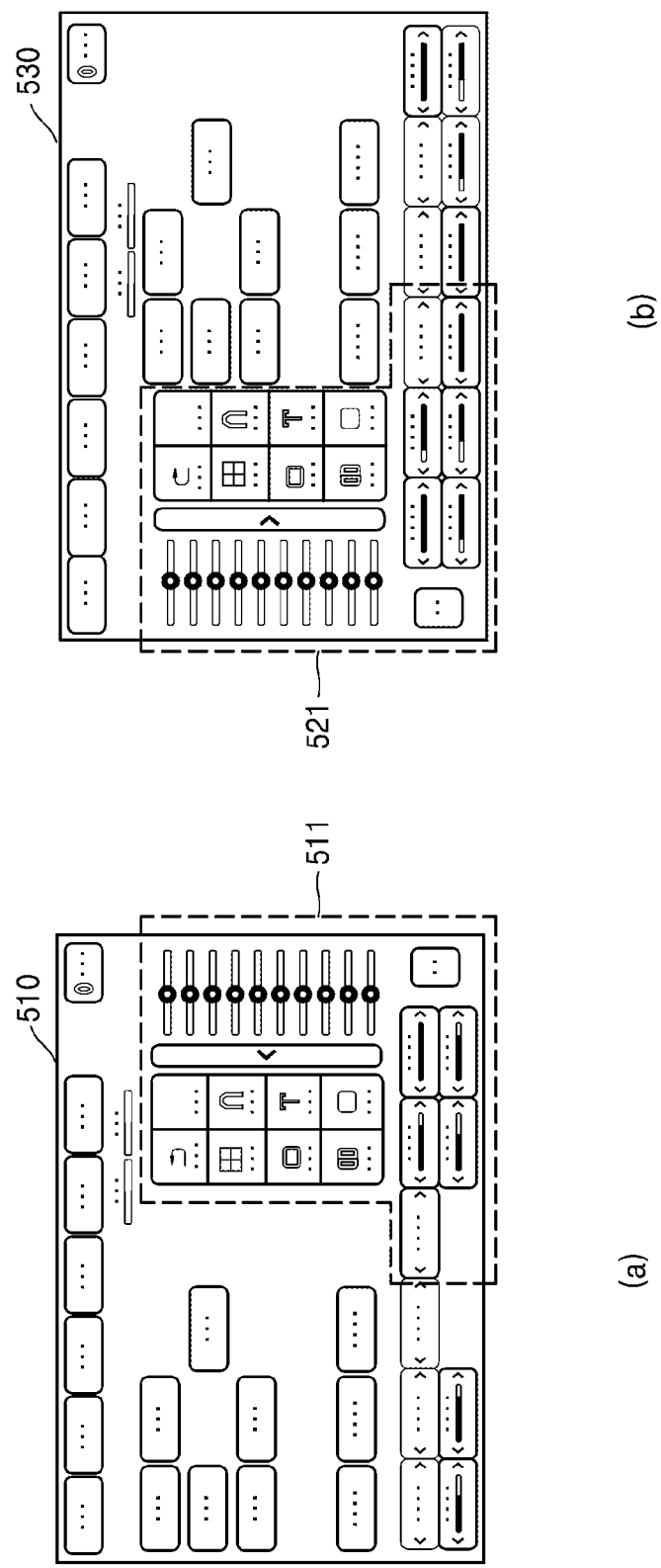

ULTRASOUND DIAGNOSIS APPARATUS, METHOD OF CONTROLLING ULTRASOUND DIAGNOSIS APPARATUS, AND STORAGE MEDIUM HAVING THE METHOD RECORDED THEREON

CROSS-REFERENCE TO RELATED PATENT APPLICATION

This application claims the benefit of U.S. Provisional Patent Application No. 62/020,645, filed on Jul. 3, 2014, in the U.S. Patent and Trademark Office, and the benefit of Korean Patent Application No. 2014-0146427, filed on Oct. 27, 2014, in the Korean Intellectual Property Office, the disclosures of which are incorporated herein in their entirety by reference.

BACKGROUND

1. Field

One or more exemplary embodiments relate to an ultrasound diagnosis apparatus capable of performing ultrasound imaging, a method of controlling the ultrasound diagnosis apparatus, and a storage medium having the method recorded thereon.

2. Description of the Related Art

Ultrasound diagnosis apparatuses irradiate an ultrasound signal generated by a transducer of a probe to an object and receives information regarding an echo signal reflected from the object, thereby obtaining an image of a part inside the object. In particular, ultrasound diagnosis apparatuses are used for medical purposes, such as observation of the inside of an object, detection of foreign substances inside the object, and diagnosis of damage thereof. Such ultrasound diagnosis apparatuses have various advantages, including stability, real-time display, and safety because there is no exposure to radiation, compared to X-ray apparatuses, and thus, the ultrasound diagnosis apparatuses are commonly used together with other image diagnosis apparatuses.

Electronic apparatuses employing a touch screen are widely used. Accordingly, ultrasound diagnosis apparatuses that interface with users via a touch screen are being developed.

There is a need to provide a method and apparatus for enabling an ultrasound diagnosis apparatus employing a touch screen to be conveniently manipulated by users.

SUMMARY

One or more exemplary embodiments include a method and apparatus for enabling an ultrasound diagnosis apparatus employing a touch screen to be conveniently manipulated by users.

Accordingly, in an ultrasound diagnosis apparatus according to an embodiment of the present invention, a method of controlling the ultrasound diagnosis apparatus, and a storage medium having the method recorded thereon, a graphical user interface (GUI) optimized for an individual user may be output on a touch screen.

Additional aspects will be set forth in part in the description which follows and, in part, will be apparent from the description, or may be learned by practice of the presented embodiments.

According to one or more embodiments of the present invention, an ultrasound diagnosis apparatus includes a touch display for displaying a GUI including a plurality of input buttons and receiving an input of a user; and a controller for detecting an input posture of the user and setting a display mode of the GUI based on the detected input posture. The GUI has a first display mode and a second display mode, and the first display mode and the second display mode are modes in which locations of at least one of the plurality of input buttons included in the GUI are differently displayed.

The at least one of the plurality of input buttons included in the GUI that is displayed in the first display mode may be disposed on a side opposite to a side on which the at least one of the plurality of input buttons included in the GUI that is displayed in the second display mode is disposed.

The input posture of the user may include a first input posture in which a left hand of the user manipulates the touch display, and a second input posture in which a right hand of the user manipulates the touch display.

The controller may set a display mode of the GUI such that the first display mode and the second display mode respectively correspond to the first input posture and the second input posture.

When the detected input posture of the user is the first input posture and the display mode of the GUI is the second display mode, the controller may change the display mode of the GUI to the first display mode. When the detected input posture of the user is the second input posture and the display mode of the GUI is the first display mode, the controller may change the display mode of the GUI to the second display mode.

The at least one of the plurality of input buttons may include at least one selected from a time gain compensation (TGC) button, a Freeze button, a Save button, a B mode button, a Color mode button, a pulse wave (PW) Doppler mode button, and a motion (M) mode.

The controller may determine the at least one of the plurality of input buttons, based on a user input.

The controller may detect the number of times each of the plurality of input buttons is used, and determine the at least one of the plurality of input buttons, based on the detected numbers of times.

The controller may set the number of the plurality of input buttons included in the GUI, the types of the plurality of input buttons, and the positions of the plurality of input buttons, based on an external input of the user.

When the touch display is positioned on a left side of a probe for detecting an ultrasound wave signal, the controller may detect the input posture of the user as the first input posture. When the touch display is positioned on a right side of the probe, the controller may detect the input posture of the user as the second input posture.

The ultrasound diagnosis apparatus may further include a sensor which senses a position of at least one selected from the probe and the touch display. The controller may detect the input posture of the user by using the sensor.

The sensor may include at least one selected from a radio frequency identification (RFID) sensor, an infrared sensor, an inclination sensor, an ultrasound sensor, and a photosensor.

When a motion defined by a predetermined pattern is sensed by a probe and the controller receives a predetermined signal from the probe, the controller may change the display mode of the GUI from one mode to another mode.

The predetermined pattern may include a predetermined number or more of consecutive horizontal or vertical movements of the probe by a predetermined distance or more.

The controller may change the GUI from one display mode to another display mode, based on a display mode change request of the user.

The ultrasound diagnosis apparatus may further include a camera which photographs the user. The controller may receive an image from the camera and detect the input posture of the user based on the image.

According to one or more embodiments of the present invention, a method of controlling an ultrasound diagnosis apparatus includes displaying a GUI including a plurality of input buttons; detecting an input posture of a user; and setting a display mode of the GUI based on the detected input posture.

The GUI may have a first display mode and a second display mode, and the first display mode and the second display mode may be modes in which locations of at least one of the plurality of input buttons included in the GUI are differently displayed.

According to one or more embodiments of the present invention, a computer-readable recording medium has recorded thereon a program for executing the method of controlling the ultrasound diagnosis apparatus.

According to one or more embodiments of the present invention, an ultrasound diagnosis apparatus includes a control panel which selects a measurement mode and a function of the ultrasound diagnosis apparatus and operates the ultrasound diagnosis apparatus according to the selected measurement mode and the selected function; a touch display which is detachable from the control panel, displays a GUI including a plurality of input buttons, and receives an input of a user; and a controller which detects an input posture of the user and sets a display mode of the GUI based on the detected input posture. The GUI has a first display mode and a second display mode, and the first display mode and the second display mode are modes in which locations of at least one of the plurality of input buttons included in the GUI are differently displayed.

According to one or more embodiments of the present invention, an ultrasound diagnosis apparatus includes a touch display which displays a GUI including a plurality of input buttons and receives an input of a user; and a controller which detects an input posture of the user and sets a display mode of the GUI based on the detected input posture. The GUI includes a plurality of modes, and the plurality of input buttons included in the GUI are displayed differently between the plurality of modes.

BRIEF DESCRIPTION OF THE DRAWINGS

These and/or other aspects will become apparent and more readily appreciated from the following description of the embodiments, taken in conjunction with the accompanying drawings in which:

FIG. 5A illustrates display modes of a graphical user interface (GUI);

DETAILED DESCRIPTION

Although general terms widely used at present were selected for describing the present invention in consideration of the functions thereof, these general terms may vary according to intentions of one of ordinary skill in the art, case precedents, the advent of new technologies, and the like. Terms arbitrarily selected by the applicant of the present invention may also be used in a specific case. In this case, their meanings need to be given in the detailed description of the present invention. Hence, the terms must be defined based on their meanings and the content of the entire specification, not by simply stating the terms.

The terms "comprises" and/or "comprising" or "includes" and/or "including" when used in this specification, specify the presence of stated elements, but do not preclude the presence or addition of one or more other elements. The terms " . . . unit" and " . . . module" when used in this specification refers to a unit in which at least one function or In operation is performed, and may be implemented as hardware, software, or a combination of hardware and software.

Throughout the specification, an "ultrasound image" refers to an image of an object that is acquired using ultrasound waves. Furthermore, an "object" may include a human, an animal, or a part of a human or animal. For example, the object may include an organ (for example, the liver, the heart, the womb, the brain, breasts, or the abdomen), blood vessels, or a combination thereof. The object may be a phantom. The phantom means a material having a density, an effective atomic number, and a volume that are approximately the same as those of a living thing.

Throughout the specification, a "user" may be, but is not limited to, a medical professional, such as a medical doctor, a nurse, a medical laboratory technologist, a medical image expert, and an engineer who repairs a medical apparatus.

Embodiments now will be described more fully hereinafter with reference to the accompanying drawings.

Figure 1:
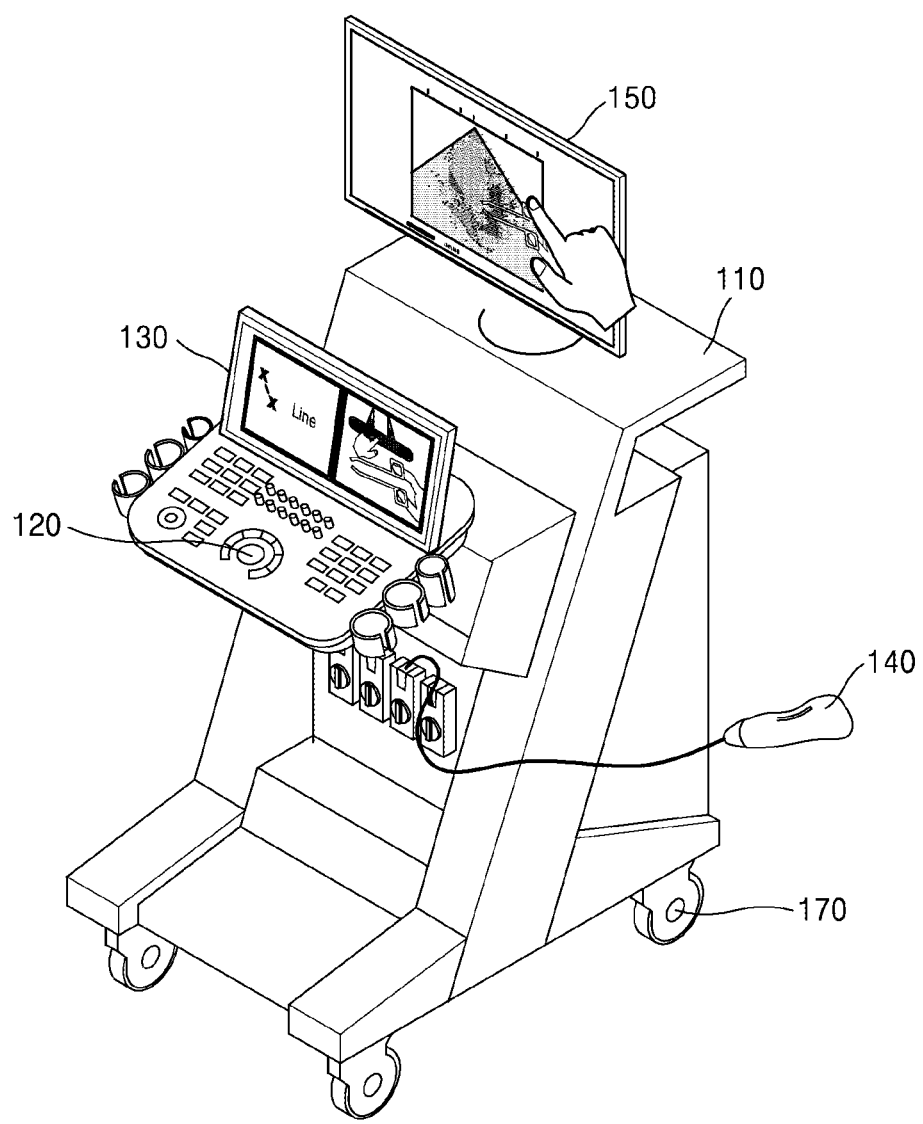
FIG. 1 is a perspective view of an ultrasound diagnosis apparatus according to an embodiment of the present invention.

FIG. 1 is a perspective view of an ultrasound diagnosis apparatus 100 according to an embodiment of the present invention.

Referring to FIG. 1, the ultrasound diagnosis apparatus 100 may include a controller (not shown), a main device 110, a control panel 120, a probe 140, and at least one display, namely, displays 130 and 150. However, all of the illustrated components are not essential. The ultrasound diagnosis apparatus 100 may be implemented by more or less components than those illustrated in FIG. 1.

In detail, the ultrasound diagnosis apparatus 100 may include at least one selected from a touch display 130 and a main display 150.

For example, the ultrasound diagnosis apparatus 100 may include the touch display 130 which displays a graphical user interface (GUI) including a plurality of input buttons and receives a user input, and the controller (not shown) which detects an input posture of the user and changes a display mode of the GUI based on the detected input posture. The GUI may include a plurality of display modes. In detail, the controller may receive information about an input posture of a user that is received from the probe 140, and detect the input posture of the user based on the received information. The controller may also receive information about a user input posture from an external apparatus, such as a camera (not shown) that is externally connected to the ultrasound diagnosis apparatus 100 and photographs a user. Based on the received information about the user input posture, the controller may detect the user input posture.

The ultrasound diagnosis apparatus 100 may further include a sensing unit (not shown). The sensing unit included in the ultrasound diagnosis apparatus 100 may detect the input posture of the user. In detail, the sensing unit may detect the input posture of the user by sensing at least one selected from a location of the probe 140, a posture of the user, and a location of the touch display 130. The sensing unit will now be described in detail.

In detail, a GUI has a first display mode or a second display mode. The first display mode and the second display mode may be modes in which locations of some of a plurality of input buttons included in the GUI are differently displayed.

The main display 150 may mainly display an ultrasound image that is captured by the ultrasound diagnosis apparatus 100.

The control panel 120 may select a measurement mode and a function of the ultrasound diagnosis apparatus 100 and operate the ultrasound diagnosis apparatus 100 according to the selected measurement mode and the selected function.

The touch display 130 may be implemented by using a touch screen, and thus may display a user interface (UI) screen image and receive a user input, for example, a touch, via the displayed UI screen image. The touch display 130 may receive at least one touch input via a body part (e.g., a finger including a thumb) of the user or a touchable input unit (e.g., a stylus pen or an electronic pen). An input applied to the touch display 130 may occur not only when a user physically contacts his or her finger or an input tool, such as a stylus pen, with the touch display 130, but also may occur in a floating touch state where the user electrically contacts the touch display 130 by closely approaching the touch display 130, i.e., a proximity contact.

The touch display 130 may display a GUI including a plurality of input buttons. The user may adjust the ultrasound image that is displayed on the main display 150, by touching the plurality of input buttons included in the GUI displayed on the touch display 130. The plurality of input buttons will be described later with reference to FIG. 5.

When a GUI convenient to manipulate the touch display 130 with the right hand is provided to a user who manipulates the touch display 130 with the left hand without regard to an input posture of the user, the user suffers inconveniences when manipulating the GUI. When a uniform GUI is provided regardless of the location of a user, the user suffers inconveniences when manipulating the ultrasound diagnosis apparatus 100 at a certain location. Accordingly, the ultrasound diagnosis apparatus 100 according to an embodiment of the present invention provides a GUI individually optimized to a user who performs ultrasonic scanning, in consideration of an input posture of the user, thereby increasing the convenience of users.

In detail, according to an embodiment of the present invention, when a GUI displayed on the touch display 130 is not suitable for an input posture of a user, the display mode of the GUI is changed to another display mode so that the user may manipulate the touch display 130 in a more comfortable posture. For example, when the user manipulates the touch display 130 with the left hand and manipulate the probe 140 with the right hand, the display mode of the GUI displayed on the touch display 130 may be automatically changed such that it is convenient for the user to manipulate the touch display 130 with the left hand.

The touch display 130 may be attached to the control panel 120 or may be disposed apart from the control panel 120. As illustrated in FIG. 1, the ultrasound diagnosis apparatus 100 may further include wheels 170 for movement.

The touch display 130 and the control pad 120 may serve as input devices for receiving user inputs.

The probe 140 is an ultrasound probe that includes a plurality of transducers and is capable of transmitting or receiving an ultrasound signal. The probe 140 may be connected to a smartphone or another medical apparatus via wire or wirelessly and thus may transmit or receive certain information thereto or therefrom. In detail, the probe 140 may be a wireless probe capable of transmitting or receiving certain data via wireless communications. Examples of the wireless probe may include, but are not limited to, a wireless probe using WIFI and a wireless probe using Bluetooth.

The probe 140 may include a sensing unit (not shown). The sensing unit of the probe 140 may sense a location, a shape, a gesture, or the like of a hand of a user that grabs the probe 140. In detail, the sensing unit of the probe 140 may include a radio frequency identification (RFID) sensor, an infrared sensor, an inclination sensor, an ultrasound sensor, a photosensor, or the like. The sensing unit of the probe 140 may acquire information used to determine whether the user manipulates the probe 140 with the left hand or the right hand, by sensing the location, the shape, the gesture, or the like of the hand of the user. The ultrasound diagnosis apparatus 100 according to an exemplary embodiment of the present invention may detect the input posture of the user, based information corresponding to a result of the sensing of the sensing unit received from the probe 140. The wireless probe will be further described later with reference to FIG. 15.

Figure 2A:
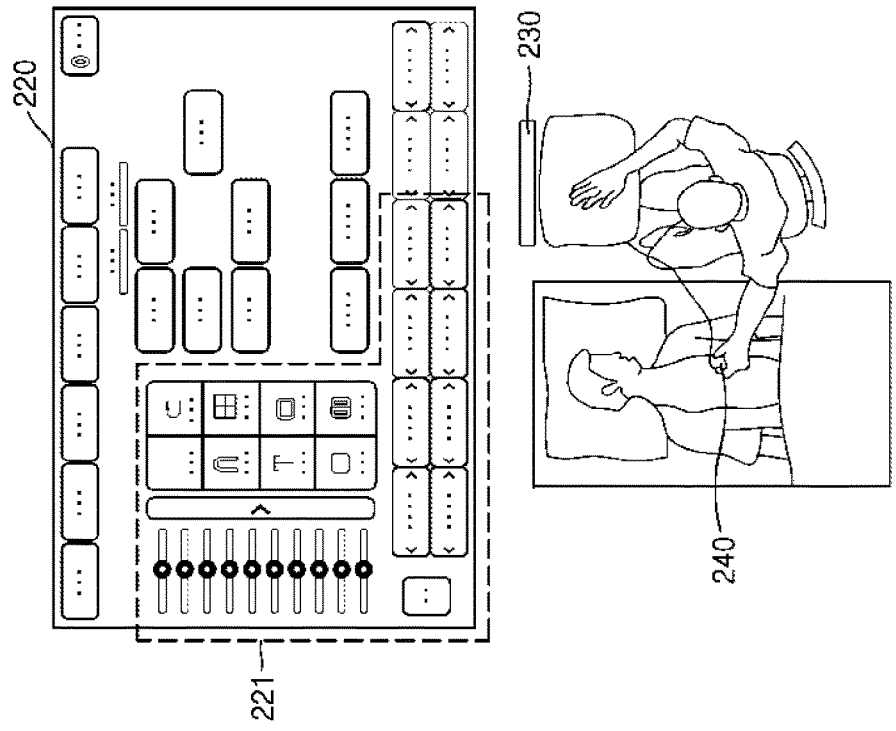
FIGS. 2A and 2B illustrate input postures of a user who uses an ultrasound diagnosis apparatus according to an embodiment of the present invention.
Figure 2B:
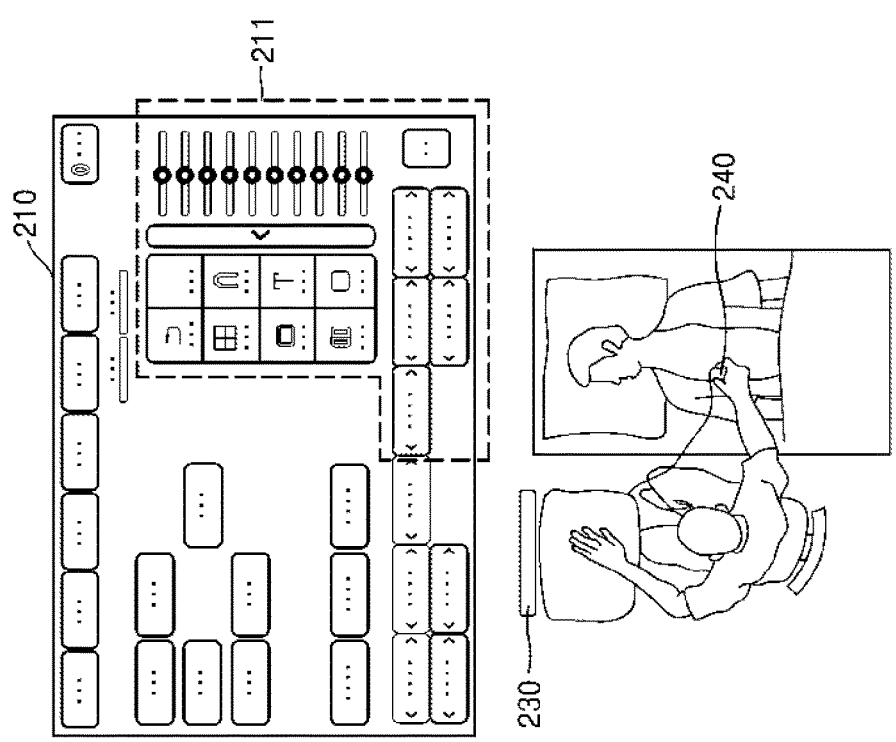

FIGS. 2A and 2B illustrate input postures of a user who uses the ultrasound diagnosis apparatus 100. The input postures of the user may include a first input posture in which the left hand of the user manipulates a touch display 230, and a second input posture in which the right hand of the user manipulates the touch display 230. The touch display 230 and a probe 240 may respectively correspond to the touch display 130 and the probe 140 of FIG. 1.

The controller (not shown) of the ultrasound diagnosis apparatus 100 may change a GUI display mode such that the first display mode and the second display mode respectively correspond to the first input posture and the second input posture.

In detail, a plurality of input buttons included in a GUI that is displayed in the first display mode may be disposed on a side opposite to the side on which a plurality of input buttons included in a GUI that is displayed in the second display mode are disposed.

FIG. 2A illustrates the first input posture in which the user manipulates the touch display 230 with the left hand and manipulates the probe 240 with the right hand. The user may manipulate the touch display 230 in order to adjust the ultrasound image that is displayed on the main display 150.

A GUI displayed on the touch display 230 may include a plurality of display modes. For example, the GUI may include a first display mode or a second display mode. Although only two display modes are illustrated as the display modes of a GUI in FIGS. 2A and 2B, embodiments are not limited thereto, and three or more display modes may be used.

A GUI displayed on the touch display 230 when the touch display 230 is manipulated with the left hand may be in a first display mode 210. Buttons mainly manipulated in the first display mode 210 may be positioned on a right side 211 of the GUI displayed on the touch display 230. In this case, the user is able to manipulate the mainly-manipulated buttons positioned on the right side 211 of the GUI displayed on the touch display 230 with the left hand without needing to move his or her body too much to the left, while manipulating the probe 240 with the right hand.

FIG. 2B illustrates the second input posture in which the user manipulates the touch display 230 with the right hand and manipulates the probe 240 with the left hand. A GUI displayed on the touch display 230 when the touch display 230 is manipulated with the right hand may be in a second display mode 220. Buttons mainly manipulated in the second display mode 220 may be positioned on a left side 221 of the GUI displayed on the touch display 230. In this case, the user is able to manipulate the mainly-manipulated buttons positioned on the left side 221 of the GUI displayed on the touch display 230 with the right hand without needing to move his or her body too much to the right, while manipulating the probe 240 with the left hand. In other words, in the first display mode 210 and the second display mode 220 of FIGS. 2A and 2B, the mainly-modulated buttons are positioned differently according to postures of the user.

The ultrasound diagnosis apparatus 100 may detect a posture of the user. For example, when the touch display 230 is positioned on the left side of the probe 240, the ultrasound diagnosis apparatus 100 may detect the input posture of the user as the first input posture, and, when the touch display 230 is positioned on the right side of the probe 240, the ultrasound diagnosis apparatus 100 may detect the input posture of the user as the second input posture.

The sensing unit included in the ultrasound diagnosis apparatus 100 may include a sensor (not shown) which senses at least one selected from a location of the probe 140, a posture of a user, and a location of the touch display 130 in order to detect an input posture of the user. In this case, the ultrasound diagnosis apparatus 100 may detect the input posture of the user by using the sensor. The sensor may include an RFID sensor, an infrared sensor, an inclination sensor, an ultrasound sensor, a photosensor, or the like. For example, when a control panel and a probe of an ultrasound diagnosis apparatus respectively include an RFID antenna and an RFID tag, the ultrasound diagnosis apparatus may ascertain a relative position of the probe with respect the control panel by sensing via the RFID antenna a direction in which a signal is transmitted by the RFID tag included in the probe.

When the GUI displayed on the touch display 230 is not appropriate for a manipulation posture of a user, the ultrasound diagnosis apparatus 100 may change the display mode of the GUI to increase the convenience of the user. For example, when the detected input posture of the user is the first input posture of FIG. 2A and the display mode of the GUI is the second display mode 220, the ultrasound diagnosis apparatus 100 may change the display mode of the GUI to the first display mode 210. On the other hand, when the detected input posture of the user is the second input posture of FIG. 2B and the display mode of the GUI is the first display mode 210, the ultrasound diagnosis apparatus 100 may change the display mode of the GUI to the second display mode 220.

The input devices 120 and 130 of the ultrasound diagnosis apparatus 100 may receive a user input that requests a change of the display mode of the GUI. Then, the controller of the ultrasound diagnosis apparatus 100 may change the display mode of the GUI according to the user input.

Figure 3:
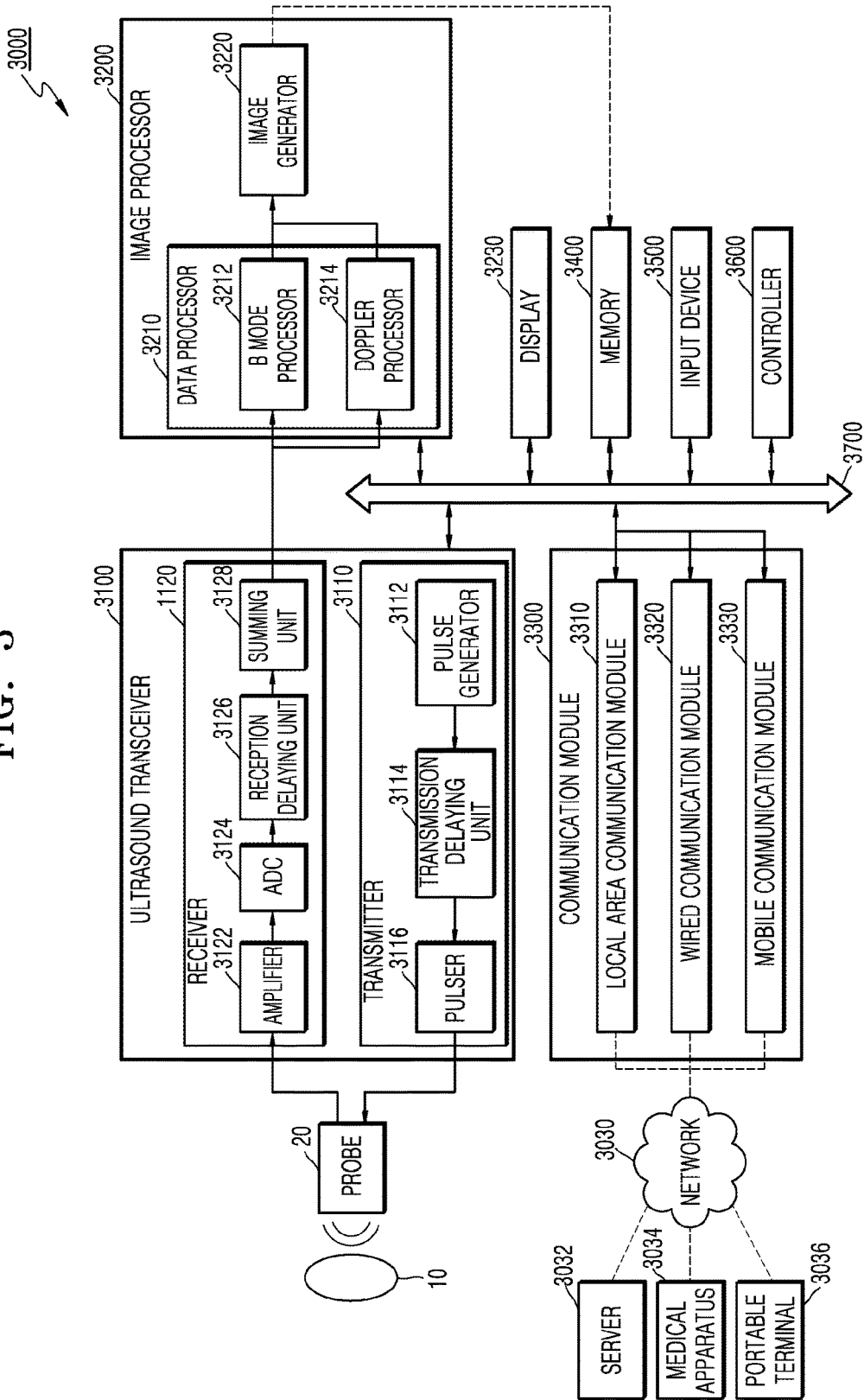
FIG. 3 is a block diagram of an ultrasound diagnosis apparatus according to an embodiment of the present invention.

FIG. 3 is a block diagram of an ultrasound diagnosis apparatus 3000 according to an embodiment of the present invention. Referring to FIG. 3, the ultrasound diagnosis apparatus 3000 may include a probe 20, an ultrasound transceiver 3100, an image processor 3200, a communication module 3300, a memory 3400, an input device 3500, and a controller 3600, which may be connected to one another via buses 3700.

In detail, the ultrasound diagnosis apparatus 3000 may correspond to the ultrasound diagnosis apparatus 100 of FIG. 1. The probe 20 may correspond to the probe 140 of FIG. 1. The controller 3600 may correspond to the controller (not shown) described above with reference to FIG. 1. A display 3230 may correspond to the main display 150 of FIG. 1. The input device 3500 may correspond to the touch display 130 of FIG. 1.

The ultrasound diagnosis apparatus 3000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 3100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 3000 by wire or wirelessly. According to embodiments of the present invention, the ultrasound diagnosis apparatus 3000 may include a plurality of probes 20.

A transmitter 3110 supplies a driving signal to the probe 20. The transmitter 3110 includes a pulse generator 3112, a transmission delaying unit 3114, and a pulser 3116. The pulse generator 3112 generates pulses for forming transmission ultrasound waves based on a predetermined pulse repetition frequency (PRF), and the transmission delaying unit 3114 delays the pulses by delay times necessary for determining transmission directionality. The pulses which have been delayed correspond to a plurality of piezoelectric vibrators included in the probe 20, respectively. The pulser 3116 applies a driving signal (or a driving pulse) to the probe 20 based on timing corresponding to each of the pulses which have been delayed.

A receiver 3120 generates ultrasound data by processing echo signals received from the probe 20. The receiver 3120 may include an amplifier 3122, an analog-to-digital converter (ADC) 1124, a reception delaying unit 3126, and a summing unit 3128. The amplifier 3122 amplifies echo signals in each channel, and the ADC 3124 performs analog-to-digital conversion with respect to the amplified echo signals. The reception delaying unit 3126 delays digital echo signals output by the ADC 3124 by delay times necessary for determining reception directionality, and the summing unit 3128 generates ultrasound data by summing the echo signals processed by the reception delaying unit 3126. Also, according to embodiments of the present invention, the receiver 3120 may not include the amplifier 3122. In other words, if the sensitivity of the probe 20 or the capability of the ADC 3124 to process bits is enhanced, the amplifier 3122 may be omitted.

The image processor 3200 generates an ultrasound image by scan-converting ultrasound data generated by the ultrasound transceiver 3100 and displays the ultrasound image. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 3212 extracts B mode components from ultrasound data and processes the B mode components. An image generator 3220 may generate an ultrasound image indicating signal intensities as brightness based on the extracted B mode components.

Similarly, a Doppler processor 3214 may extract Doppler components from ultrasound data, and the image generator 3220 may generate a Doppler image indicating a movement of an object as colors or waveforms based on the extracted Doppler components.

According to an embodiment of the present invention, the image generator 3220 may generate a three-dimensional (3D) ultrasound image via volume-rendering with respect to volume data and may also generate an elasticity image by imaging deformation of the object 10 due to pressure. Furthermore, the image generator 3220 may display various pieces of additional information in an ultrasound image by using text and graphics. In addition, the generated ultrasound image may be stored in the memory 3400.

The display 3230 displays the generated ultrasound image. The display 3230 may display not only an ultrasound image, but also various pieces of information processed by the ultrasound diagnosis apparatus 3000 on a screen image via a graphical user interface (GUI). In addition, the ultrasound diagnosis apparatus 3000 may include two or more displays 1400 according to embodiments of the present invention.

The communication module 3300 is connected to a network 3030 by wire or wirelessly to communicate with an external device or a server. The communication module 3300 may exchange data with a hospital server or another medical apparatus in a hospital, which is connected thereto via a PACS. Furthermore, the communication module 3300 may perform data communication according to the digital imaging and communications in medicine (DICOM) standard.

The communication module 3300 may transmit or receive data related to diagnosis of an object, e.g., an ultrasound image, ultrasound data, and Doppler data of the object, via the network 3030 and may also transmit or receive medical images captured by another medical apparatus, e.g., a computed tomography (CT) apparatus, a magnetic resonance imaging (MRI) apparatus, or an X-ray apparatus. Furthermore, the communication module 3300 may receive information about a diagnosis history or medical treatment schedule of a patient from a server and utilizes the received information to diagnose the patient. Furthermore, the communication module 3300 may perform data communication not only with a server or a medical apparatus in a hospital, but also with a portable terminal of a medical doctor or patient.

The communication module 3300 is connected to the network 3030 by wire or wirelessly to exchange data with a server 3032, a medical apparatus 34, or a portable terminal 36. The communication module 3300 may include one or more components for communication with external devices. For example, the communication module 3300 may include a close-distance communication module 3310, a wired communication module 3320, and a mobile communication module 3330.

The close-distance communication module 3310 refers to a module for close-distance communication within a predetermined distance. Examples of close-distance communication techniques according to an embodiment of the present invention may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 3320 refers to a module for communication using electric signals or optical signals. Examples of wired communication techniques according to an embodiment of the present invention may include communication via a twisted pair cable, a coaxial cable, an optical fiber cable, and an Ethernet cable.

The mobile communication module 3330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 3400 stores various data processed by the ultrasound diagnosis apparatus 3000. For example, the memory 3400 may store medical data related to diagnosis of an object, such as ultrasound data and an ultrasound image that are input or output, and may also store algorithms or programs which are to be executed in the ultrasound diagnosis apparatus 3000.

The memory 3400 may be any of various storage media, e.g., a flash memory, a hard disk drive, EEPROM, etc. Furthermore, the ultrasound diagnosis apparatus 3000 may utilize web storage or a cloud server that performs the storage function of the memory 3400 online.

The input device 3500 refers to a means via which a user inputs data for controlling the ultrasound diagnosis apparatus 3000. The input device 3500 may include hardware components, such as a keypad, a mouse, a touch pad, a touch screen, and a jog switch. However, embodiments of the present invention are not limited thereto, and the input device 3500 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The controller 3600 may control all operations of the ultrasound diagnosis apparatus 3000. In other words, the controller 3600 may control operations among the probe 20, the ultrasound transceiver 3100, the image processor 3200, the communication module 3300, the display 3230, the memory 3400, and the input device 3500.

All or some of the probe 20, the ultrasound transceiver 3100, the image processor 3200, the communication module 3300, the display 3230, the memory 3400, the input device 3500, and the controller 3600 may be implemented as software modules. However, embodiments of the present invention are not limited thereto, and some of the components stated above may be implemented as hardware modules. Furthermore, at least one selected from the ultrasound transceiver 3100, the image processor 3200, and the communication module 3300 may be included in the controller 3600. However, embodiments of the present invention are not limited thereto.

Figure 4:
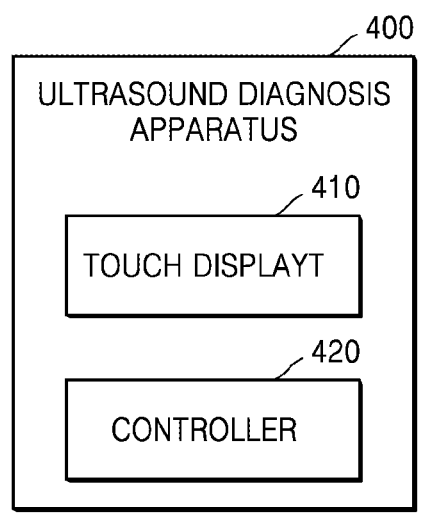
FIG. 4 is a block diagram of an ultrasound diagnosis apparatus according to an embodiment of the present invention.

FIG. 4 is a block diagram of an ultrasound diagnosis apparatus 400 according to an embodiment of the present invention.

Referring to FIG. 4, the ultrasound diagnosis apparatus 400 may include a touch display 410 and a controller 420. In detail, the ultrasound diagnosis apparatus 400 may correspond to the ultrasound diagnosis apparatus 100 of FIG. 1. In detail, the touch display 410 and the controller 420 may respectively correspond to the touch display 130 and the controller of FIG. 1.

The ultrasound diagnosis apparatus 400 may correspond to the ultrasound diagnosis apparatus 3000 of FIG. 3.

The touch display 410 may display a GUI including a plurality of input buttons and receive an input of a user. A plurality of input buttons are included in a GUI of a touch display and may be input buttons capable of adjusting an ultrasound image that is displayed on a main display. The plurality of input buttons will be further described with reference to FIG. 5A.

The controller 420 may detect an input posture of a user and change a display mode of the displayed GUI based on the detected input posture. As illustrated in FIGS. 2A and 2B, the input posture of the user may be a first input posture in which the left hand of a user manipulates a touch display, or a second input posture in which the right hand of a user manipulates a touch display. The controller 420 may correspond to the controller 3600 of FIG. 3.

The GUI may include a first display mode and a second display mode. The positions of some of the plurality of input buttons included in the GUI may be displayed differently in the first display mode than in the second display mode. For example, locations of some input buttons in the first display mode may be symmetrical with those in the second display mode. The first and second display modes will be further described with reference to FIGS. 5A-5C.

When it is determined that the display mode of the GUI is not appropriate for a current input posture of a user, the controller 420 may change the display mode of the GUI to another mode. For example, when the detected input posture of the user is the first input posture of FIG. 2A and the display mode of the GUI is the second display mode 220, the controller 420 may change the display mode of the GUI to the first display mode 210. On the other hand, when the detected input posture of the user is the second input posture of FIG. 2B and the display mode of the GUI is the first display mode 210, the controller 420 may change the display mode of the GUI to the second display mode 220.

FIG. 5A illustrates display modes of a GUI. (a) of FIG. 5A illustrates an example of a first display mode 510 from among the display modes of the GUI, and (b) of FIG. 5A illustrates an example of a second display mode 530 from among the display modes of the GUI.

In the first display mode 510, a plurality of input buttons may be arranged such that a touch display may be conveniently manipulated in the first input posture in which the left hand manipulates the touch display. In the second display mode 530, the plurality of input buttons may be arranged such that the touch display may be conveniently manipulated in the second input posture in which the right hand manipulates the touch display.

For example, a plurality of input buttons included in a GUI that is displayed in the first display mode 510 may be disposed on a side opposite to a side on which a plurality of input buttons included in a GUI that is displayed in the second display mode 530 are disposed.

In detail, in the first display mode 510, some input buttons that are mainly used from among the plurality of input buttons may be disposed on a right side 511 of the GUI. In the second display mode 530, some input buttons that are mainly used from among the plurality of input buttons may be disposed on a left side 521 of the GUI.

The GUI may include various shapes and types of input buttons in consideration of functions and operations of the ultrasound diagnosis apparatus 400. For example, the plurality of input buttons included in the GUI may include buttons for adjusting an ultrasound image, such as, a Harmonic button, a Time Gain Compensation (TGC) button, a Dual live button (i.e., simultaneous display of a 2D image and a Doppler image), a Panoramic button (i.e., a panorama view), a MultiVision button (i.e., use of a multi-beam for improving the quality of an image), a ClearVision button (i.e., removal of noise from an image), a Freeze button (i.e., a temporary stop), a Save button (i.e., storage), a B button (i.e., a 2D mode), a C button (i.e., a color mode), a PW button (i.e., a pulse wave Doppler mode—checking of a blood flow speed), a M button (i.e., a motion mode—representing a motion corresponding to a virtual line drawn in a second dimension (2D)), a Scan Area button (i.e., adjustment of the width of an image), an Angle button (i.e., adjustment of the angle of an image), a Dynamic Range button (i.e., adjustment of a contrast by adjusting a ratio between a minimum value of a maximum value of an input signal). The plurality of input buttons may also include buttons that adjust an interface, such as, a left/right (L/R) Flip button (i.e., a change of a display mode of a GUI) and a Top-Bottom Dual button (i.e., horizontal and vertical changes of a layout of input buttons on a touch screen).

For example, when a user touches a Harmonic button from among a plurality of input buttons, an Optimal Harmonic Imaging (OHI) function for optimizing an image by using a high frequency is turned on or off, and thus an ultrasound image may be adjusted.

For example, when the user touches a TGC button from among the plurality of input buttons, a gain of the ultrasound image according to a depth thereof may be adjusted. The TGC button may be used to adjust the gain of an ultrasound image according to a depth thereof in order to compensate for weakening of an ultrasound wave with a depth of the ultrasound wave. The TGC button will now be further described with reference to FIG. 5B.

Figure 5B:
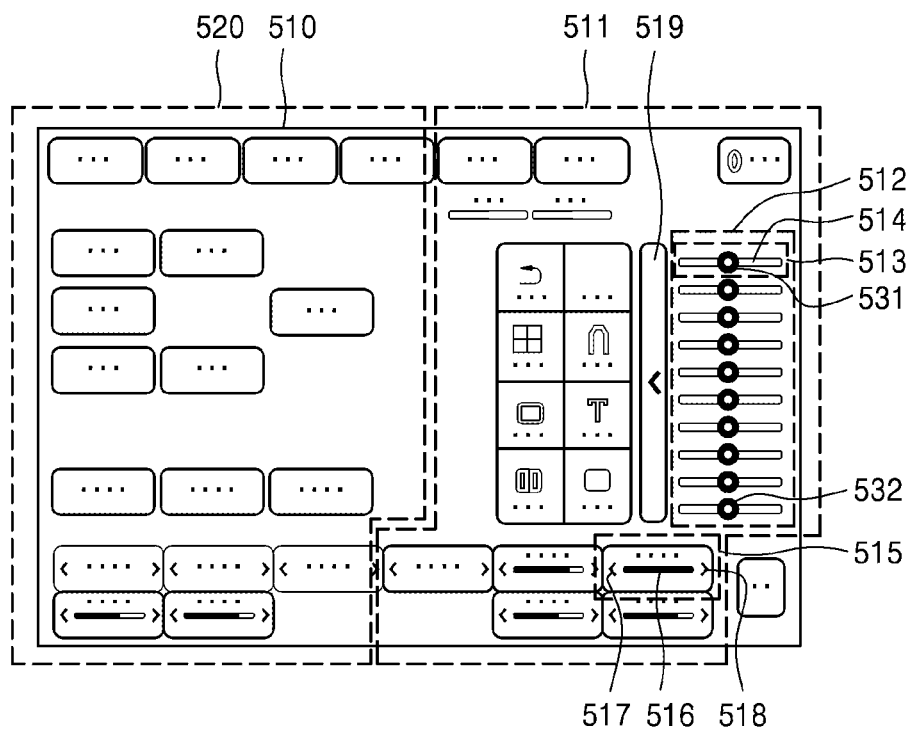
FIG. 5B illustrates input buttons included in a first display mode.

FIG. 5B illustrates the input buttons included in the first display mode 510. For example, the first display mode 510 may be a display mode corresponding to a user who manipulates a GUI with the left hand. Alternatively, the first display mode 510 may be a display mode that is provided when a user is located on the right side of the touch display 410.

Referring to FIG. 5B, the first display mode 510 may be divided into an area 511 for displaying frequently-used buttons and an area 520 for displaying infrequently-used buttons.

In the area 511 for displaying frequently-used buttons, some buttons that are frequently used to manipulate an image may be disposed.

The buttons that are frequently used to manipulate an image may be, for example, a TGC area 512, a Freeze button (i.e., a temporary stop), a Save button (i.e., storage), a B button (i.e., a 2D mode), a C button (i.e., a color mode), a PW button (i.e., a pulse wave Doppler mode—checking of a blood flow speed), a M button (i.e., a motion mode—representing a motion corresponding to a virtual line drawn in a second dimension (2D)), and a scan area 515 (i.e., adjustment of a scan area).

In the first display mode 510, a method of manipulating input buttons may be changed such that a user may conveniently manipulate a touch display in the first input posture in which the left hand manipulates the touch display.

For example, the TGC area 512 includes a plurality of slides, each of which may adjust a gain according to a depth. For example, an uppermost slide bar 531 in the TGC area 512 may adjust a gain of a shallowest area of an imaging area, and a lowermost slide bar 532 therein may adjust a gain of a deepest area of the imaging area. A user may move the uppermost slide bar 531 of an uppermost slid 513 capable of adjusting the gain by using a touch.

At this time, according to input postures of the user, a variation in a gain according to a moving direction of the uppermost slide bar 531 may be differently input. In detail, since the first display mode 510 corresponds to a GUI that is manipulated by the left hand of a user, the gain may be set to increase when the uppermost slide bar 531 moves from the right side to the left side. On the other hand, in the second display mode 530, the gain may be set to increase when the uppermost slide bar 531 moves from the left side to the right side. However, embodiments of the present invention are not limited thereto, and the setting may vary according to convenience or the like of a user.

A user may touch an extension button 519, and thus the ultrasound diagnosis apparatus 400 may receive a fine adjustment by further extending the TGC area 512. Alternatively, when the extension button 519 is touched, additional input buttons may be displayed on the area 511 for displaying frequently-used buttons.

The scan area 515 may adjust a width of an ultrasound image. The user may increase or decrease the width of the ultrasound image by using a button displayed on the scan area. As the width of the ultrasound image increases, a frame rate may decrease.

In detail, as a left button 517 and a right button 518 included in the scan area 515 are touched, a slide 516 of the scan area 515 may increase or decrease. At this time, according to display modes, an increase or decrease in the slide 516 may be differently input. For example, when the left button 517 is touched in the first display mode 510, the width of the ultrasound image may be set to increase. On the other hand, in the second display mode 530, only when the right button 518 is touched, the width of the ultrasound image may increase.

Figure 5C:
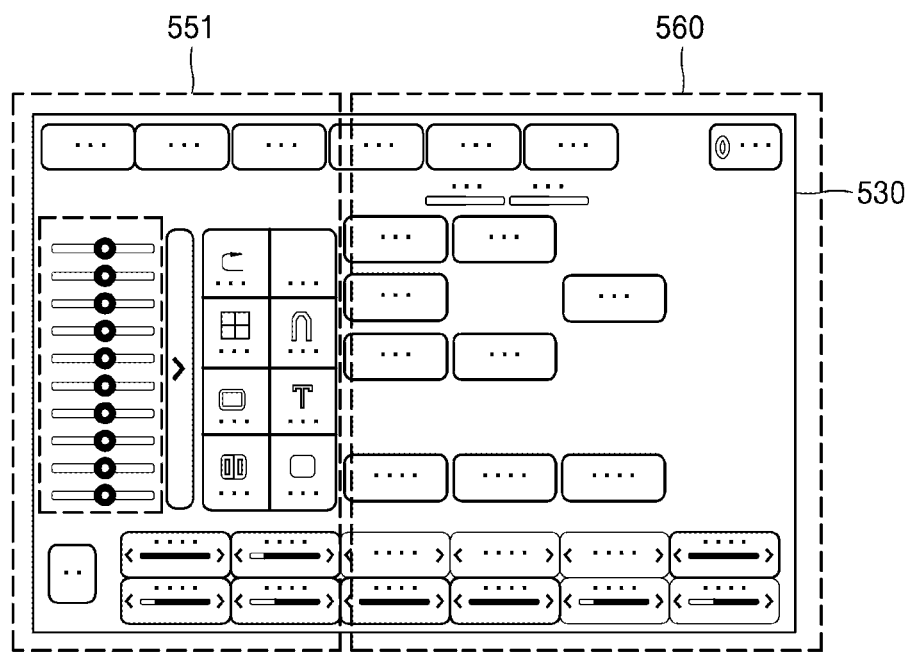
FIG. 5C illustrates input buttons included in a second display mode.

FIG. 5C illustrates input buttons included in the second display mode 530.

Referring to FIG. 5C, the second display mode 530 may be divided into an area 551 for displaying frequently-used buttons and an area 560 for displaying infrequently-used buttons.

In the second display mode 530, a plurality of input buttons may be arranged such that a user may conveniently manipulate a touch display in the second input posture in which the right hand manipulates the touch display. The locations of the plurality of input buttons arranged in the second display mode may be different from those of the plurality of input buttons arranged in the first display mode. For example, some buttons that are mainly used to manipulate an ultrasound image may be positioned on the right side of a GUI displayed in the first display mode 510, but may be positioned on the left side of a GUI displayed in the second display mode 530. In other words, the positions of the buttons that are mainly used to manipulate an ultrasound image may vary according to display modes.

The ultrasound diagnosis apparatus 400 may determine some buttons of which positions vary according to different modes, based on a user input. The user input may be made via a keyboard, a mouse, a touch screen, or the like. For example, a user may select some buttons of which positions are to be changed from among a plurality of input buttons, via a touch screen.

Moreover, the user may change the entire configuration of the plurality of input buttons. For example, the user may change the first display mode 510 and the second display mode 530 of a GUI in a manner desired by a user. For example, the user may change at least one selected from the number of plurality of input buttons, the types thereof, and the positions thereof in at least one of the first and second display modes 510 and 530. In other words, the user may reconstruct the plurality of buttons included in each of the first display mode 510 and the second display mode 530 in a desired manner.

The ultrasound diagnosis apparatus 400 may detect the number of times each of the plurality of input buttons is used, and re-determine some buttons of which positions are to be changed from among the plurality of input buttons, based on the detected numbers of times. For example, when a TGC button and a SAVE button are respectively the most frequently and second most frequently used, the TGC button and the SAVE button may be determined as the some buttons of which positions are to be changed. Thus, the TGC button and the SAVE button may be disposed on the right side in the first display mode 510 and may be disposed on the left side in the second display mode 530.

Figure 6:
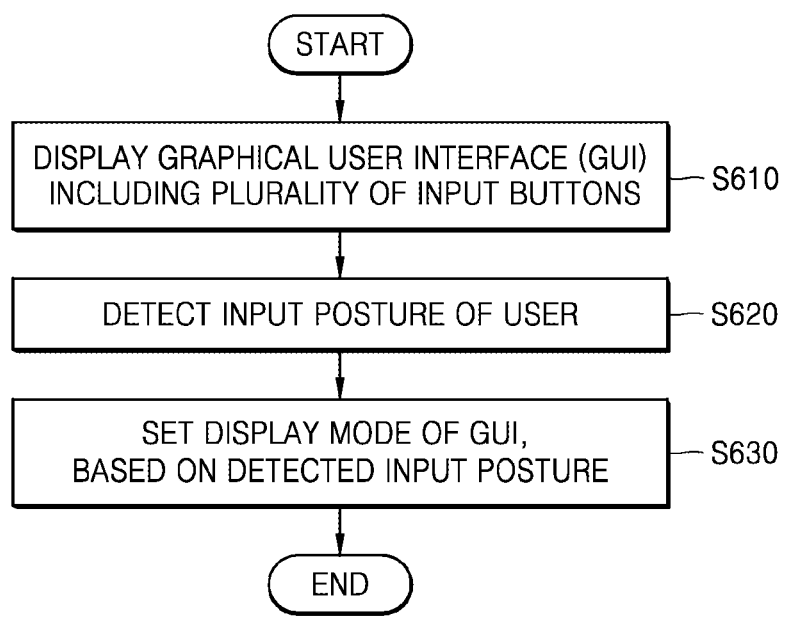
FIG. 6 is a flowchart of a method of controlling an ultrasound diagnosis apparatus, according to an embodiment of the present invention.

FIG. 6 is a flowchart of a method of controlling an ultrasound diagnosis apparatus, according to an embodiment of the present invention.

In operation S610, the ultrasound diagnosis apparatus 400 may display a GUI including a plurality of input buttons.

In operation S620, the ultrasound diagnosis apparatus 400 may detect an input posture of a user.

In operation S630, the ultrasound diagnosis apparatus 400 may set a display mode of the GUI, based on the detected input posture. The GUI may include a first display mode and a second display mode. The positions of some of the plurality of input buttons included in the GUI may be displayed differently in the first display mode than in the second display mode.

According to an embodiment, since a display mode of a GUI that enables a convenient manipulation is provided according to an input posture of a user, the user may more conveniently manipulate the input buttons of a GUI.

Figure 7:
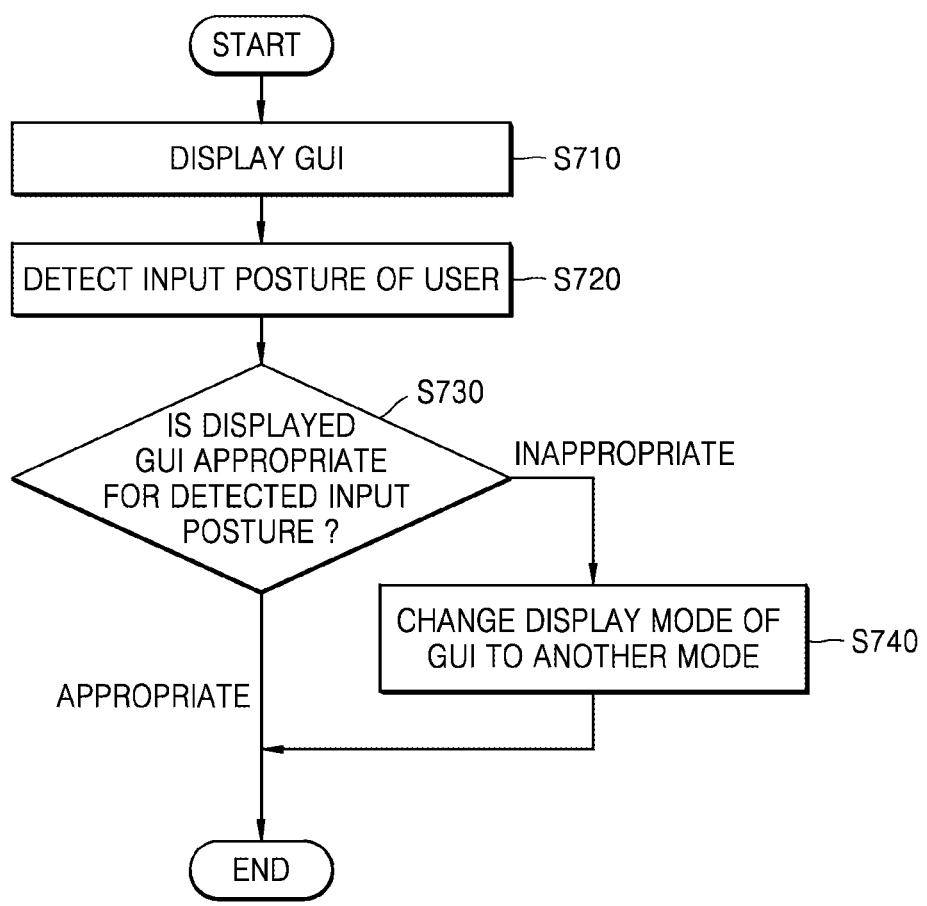
FIG. 7 is a flowchart of a process of changing a display mode of a GUI, according to an embodiment of the present invention.

FIG. 7 is a flowchart of a process of changing a display mode of a GUI, according to an embodiment of the present invention.

In operation S710, the ultrasound diagnosis apparatus 400 may display a GUI including a plurality of input buttons via a touch display. The GUI may include a first display mode and a second display mode. In the first display mode and the second display mode, the positions of some of the plurality of input buttons included in the GUI may be differently displayed.

In operation S720, the ultrasound diagnosis apparatus 400 may detect an input posture of a user. The input postures of the user may include a first input posture in which the left hand of the user manipulates the touch display, and a second input posture in which the right hand of the user manipulates the touch display.

In operation S730, the ultrasound diagnosis apparatus 400 may compare the detected input posture with the displayed GUI. For example, the comparison may denote a determination as to whether the display mode of the GUI is the first display mode when the detected input posture is the first input posture, or a determination as to whether the display mode of the GUI is the second display mode when the detected input posture is the second input posture. At this time, the ultrasound diagnosis apparatus 400 may determine that the display mode of the GUI is appropriate for the detected input posture. When the displayed GUI is appropriate for the detected input posture, the ultrasound diagnosis apparatus 400 may conclude the process of FIG. 7 without changing the display mode of the GUI.

On the other hand, when the displayed GUI is inappropriate for the detected input posture, for example, when the detected input posture is the first input posture and the display mode of the GUI is the second display mode or when the detected input posture is the second input posture and the display mode of the GUI is the first display mode, the process proceeds to operation S740.

The determination as to whether the displayed GUI is appropriate or inappropriate for the user may be performed by the controller 420. In detail, the controller determines the suitability of the GUI, based on information about a user input posture sensed by a sensing unit (not shown) or information about a user input posture received from an external source or acquired by the controller 420. Alternatively, the controller 420 may determine the suitability of the GUI, based on a user input. In detail, when a user requests a change of the display mode of the GUI, the controller 420 may determine that the displayed GUI is inappropriate.

In operation S740, the ultrasound diagnosis apparatus 400 may change the display mode of the GUI to another mode. For example, when the display mode of the current GUI is the first display mode, the ultrasound diagnosis apparatus 400 may change the display mode of the current GUI to the second display mode, and, when the display mode of the current GUI is the second display mode, the ultrasound diagnosis apparatus 400 may change the display mode of the current GUI to the first display mode.

Figure 8:
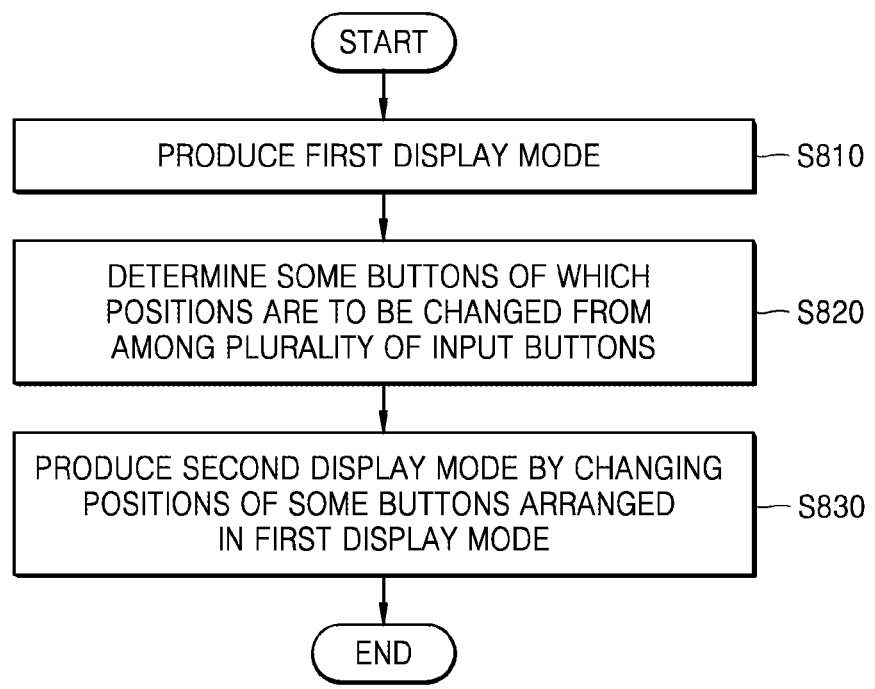
FIG. 8 is a flowchart of a process of producing a first display mode and a second display mode which are display modes of a GUI.

FIG. 8 is a flowchart of a process of producing a first display mode and a second display mode which are display modes of a GUI.

In operation S810, the ultrasound diagnosis apparatus 400 may produce a plurality of input buttons corresponding to a first display mode. The plurality of input buttons corresponding to the first display mode may be previously stored in the ultrasound diagnosis apparatus 400.

In operation S820, the ultrasound diagnosis apparatus 400 may determine some buttons of which positions are to be changed from among the plurality of input buttons.

According to an embodiment, buttons that are frequently used to manipulate an ultrasound image may be previously determined as the some buttons and stored in a memory of the ultrasound diagnosis apparatus 400.

According to another embodiment, the some buttons of which positions are to be changed from among the plurality of input buttons may be determined based on an input of a user. For example, the user may directly determine the some buttons of which positions are to be changed, via an input device such as a touch display, a mouse, or a keyboard.

According to another embodiment, the some buttons of which positions are to be changed may be determined based on the number of times each of the plurality of input buttons is used. For example, the ultrasound diagnosis apparatus 400 may determine a predetermined number of frequently-used buttons, as the some buttons of which positions are to be changed.

Even after the some buttons of which positions are to be changed are determined, the some buttons may be re-determined by an external input of a user. For example, the user may re-determine the some buttons of which positions are to be changed, via a touch display, a mouse, a keyboard, or the like. For example, when buttons A, B, and C are initially set as the some buttons of which positions are to be changed and later the user determines buttons E and F as the some buttons of which positions are to be changed, only the positions of the buttons E and F may be changed when the display mode of a GUI is changed, despite the initial setting.

In operation S830, the ultrasound diagnosis apparatus 400 may produce the second display mode by changing the positions of the some buttons arranged in the first display mode. For example, the second display mode may be produced such that some buttons positioned on the right side of a screen image in the first display mode are positioned on the left side of the screen image in the second display mode.

Figure 9:
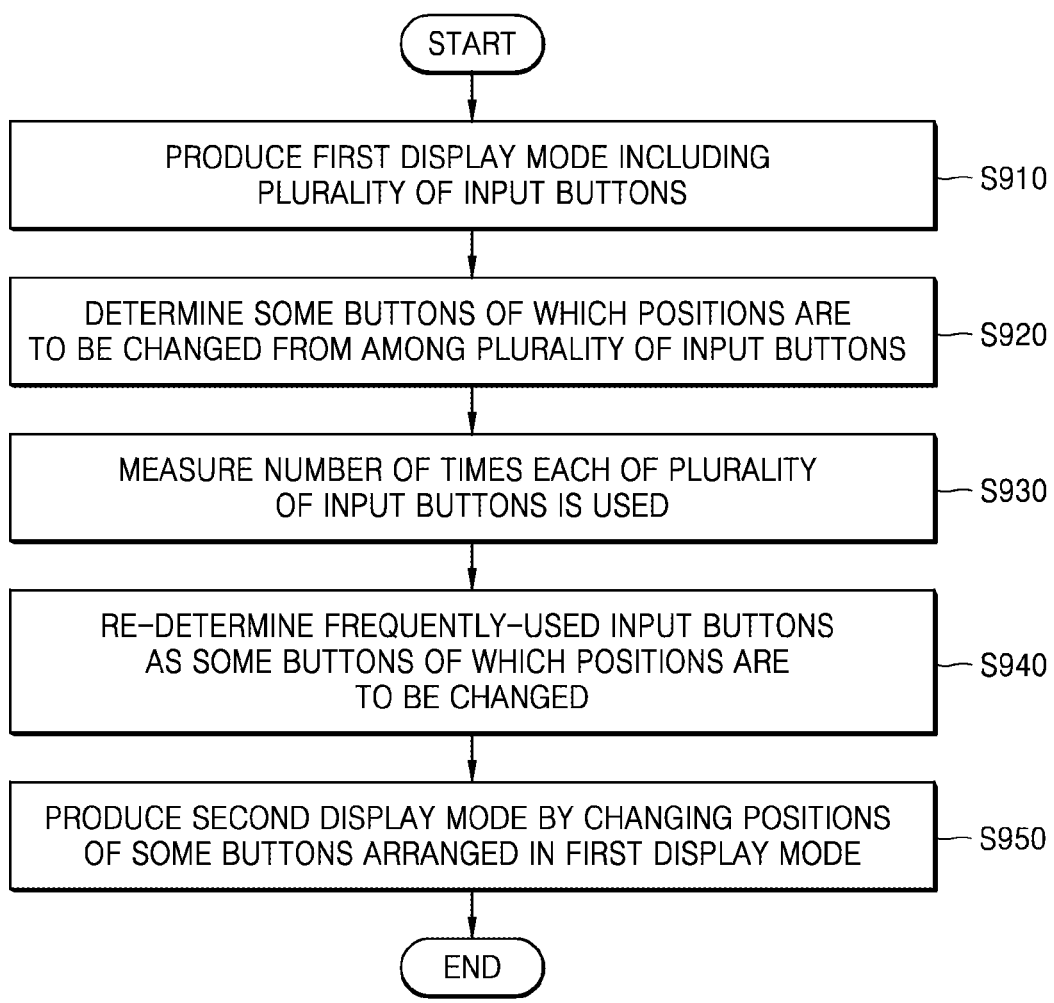
FIG. 9 is a flowchart of a process of re-determining some buttons of which positions are to be changed from among a plurality of input buttons by measuring the number of times each of the plurality of input buttons is used, according to an embodiment of the present invention.

FIG. 9 is a flowchart of a process of re-determining some buttons of which positions are to be changed from among a plurality of input buttons by measuring the number of times each of the plurality of input buttons is used, according to an embodiment of the present invention.

In operation S910, the ultrasound diagnosis apparatus 400 may produce a first display mode including a plurality of input buttons.

In operation S920, the ultrasound diagnosis apparatus 400 may determine some buttons of which positions are to be changed from among the plurality of input buttons.

In operation S930, the ultrasound diagnosis apparatus 400 may measure the number of times each of the plurality of input buttons is used. For example, the number of times each of the plurality of input buttons is used may be individually measured via an input of a touch display.

In operation S940, the ultrasound diagnosis apparatus 400 may re-determine frequently-used input buttons as the some buttons of which positions are to be changed. For example, even when buttons A, B, and C have been determined as the some buttons of which positions are to be changed in operation S920, if the measured numbers of times buttons D and E are respectively used are high, the some buttons of which positions are to be changed may be re-determined to be the buttons D and E. Since the re-determination of the some buttons of which positions are to be changed may not be the intention of a user, the re-determined buttons may be used or may not be used according to an input of the user.

In operation S950, the ultrasound diagnosis apparatus 400 may produce a second display mode by changing the positions of the some buttons arranged in the first display mode.

Figure 10:
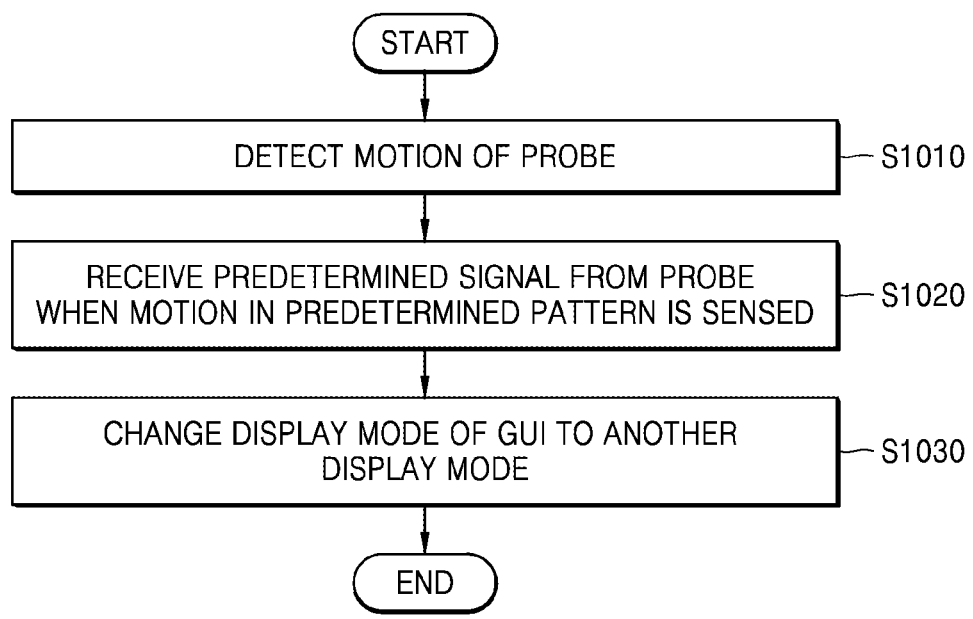
FIG. 10 is a flowchart of a process in which an ultrasound diagnosis apparatus changes a currently-displayed display mode to another display mode by sensing a motion of a probe, according to an embodiment of the present invention.

FIG. 10 is a flowchart of a process in which the ultrasound diagnosis apparatus 400 changes a currently-displayed display mode to another display mode by sensing a motion of a probe, according to an embodiment of the present invention.

In operation S1010, the ultrasound diagnosis apparatus 400 may detect a motion of a probe. For example, the ultrasound diagnosis apparatus 400 may sense the motion of the probe by using a sensor included therein. A sensor included in the probe may sense whether the probe moves horizontally or vertically. In other words, a pattern in which the probe has moved may be sensed.

In operation S1020, when the pattern in which the probe has moved is identical with a predetermined pattern, the ultrasound diagnosis apparatus 400 may receive a predetermined signal from the probe. The predetermined signal may be, for example, a wired or wireless signal used for requesting a change of the display mode.

In operation S1030, when a motion defined by a predetermined pattern is sensed by the probe and the ultrasound diagnosis apparatus 400 receives a predetermined signal from the probe, the ultrasound diagnosis apparatus 400 may change the display mode of a GUI to another display mode. For example, when the probe is determined to move in a predetermined pattern and a motion of the probe is detected, the ultrasound diagnosis apparatus 400 may change a first display mode of a touch display to a second display mode or the second display mode thereof to the first display mode. The operation S1030 will now be further described with reference to FIG. 11.

Figure 11:
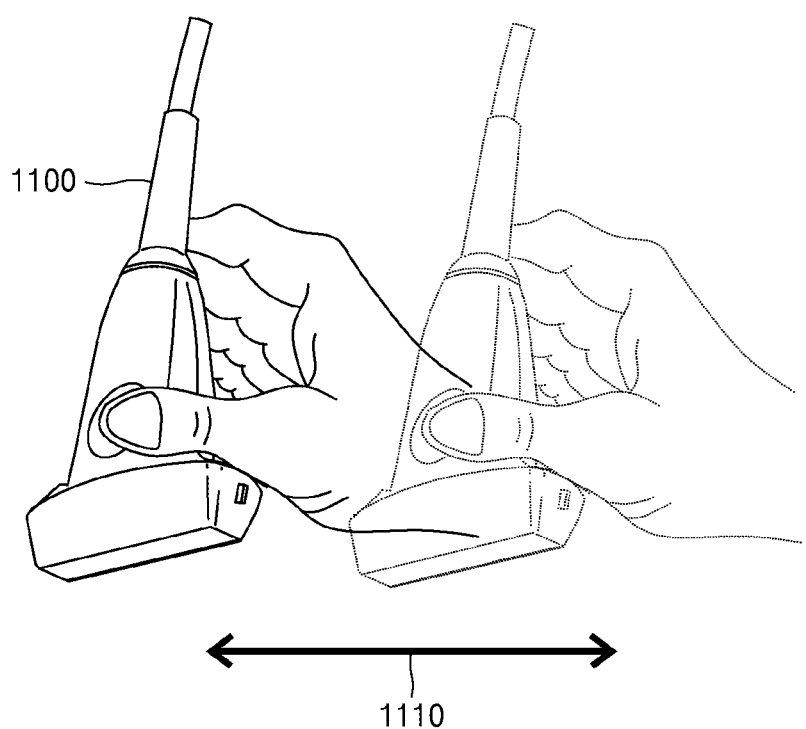
FIG. 11 illustrates a motion pattern of a probe according to an embodiment of the present invention.

FIG. 11 illustrates a motion pattern of a probe 1100 according to an embodiment of the present invention.

When a motion defined by a predetermined pattern is sensed by the probe 1100 and the ultrasound diagnosis apparatus 400 receives a predetermined signal from the probe 1100, the ultrasound diagnosis apparatus 400 may change the display mode of a GUI from a mode to another mode. A user may define the predetermined pattern used for changing a display mode. The predetermined pattern may denote a predetermined number or more of consecutive horizontal or vertical movements of the probe 1100 by a predetermined distance or more. In this case, when a movement in the predetermined pattern is sensed, the ultrasound diagnosis apparatus 400 may change the display mode.

For example, when the probe 1100 consecutively moves a predetermined number of times or more by a predetermined distance or greater in a horizontal or vertical direction, it is sensed that the probe 1100 moves, and the display mode may be changed.

However, when a motion of the probe 1100 is finely sensed, the display mode of a GUI may be unintentionally changed even when the probe 1100 is simply used.

Accordingly, to prevent an unwanted display mode change, a predetermined distance used for sensing a motion of the probe 1100 may be determined. For example, when the value of a predetermined distance by which the probe 1100 needs to horizontally move is determined to be 1, a distance 1110 by which the probe 1100 needs to repeatedly move in a horizontal direction in order to change the display mode of a GUI may be 1 cm. When the value of the predetermined distance by which the probe 1100 needs to horizontally move is determined to be 5, the distance 1110 by which the probe 1100 needs to repeatedly move in a horizontal direction in order to change the display mode of a GUI is determined to be 5 cm. Thus, a motion by the predetermined distance or less does not cause a change of the display mode. However, this predetermined distance determination is an example, and embodiments are not limited thereto.

To prevent an unwanted display mode change, the number of times a motion by at least the predetermined distance used for sensing a motion of the probe 1100 is repeated may also be pre-determined. For example, when the number of times is determined to be 5, the probe 1100 needs to repeatedly move 5 times or more in order to change the display mode of a GUI.

Figure 12:
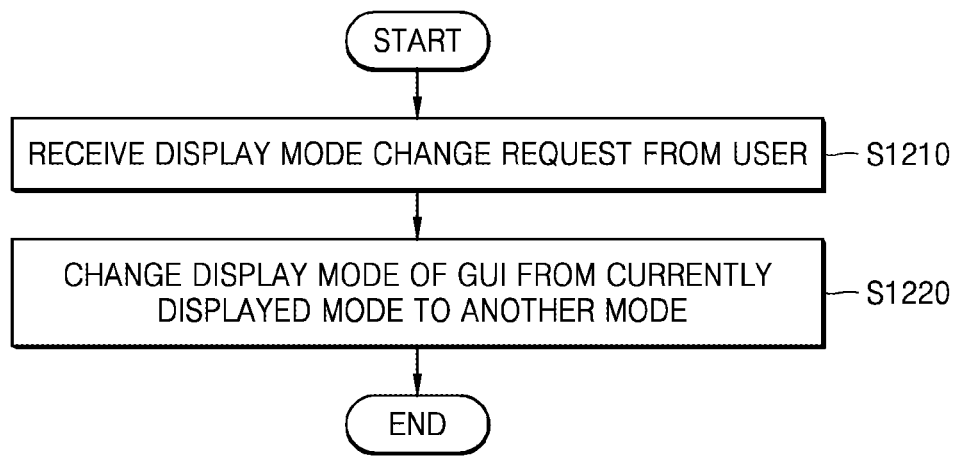
FIG. 12 is a flowchart of a process of changing a display mode according to a request of a user, according to an embodiment of the present invention.

FIG. 12 is a flowchart of a process of changing a display mode according to a request of a user, according to an embodiment of the present invention.

In operation S1210, the ultrasound diagnosis apparatus 400 may receive a display mode change request from the user. For example, the ultrasound diagnosis apparatus 400 may display a setting page on the touch display 410 and receive the display mode change request from the user via the setting page. Alternatively, the ultrasound diagnosis apparatus 400 may receive the display mode change request when the user touches a L/R flip button from among the plurality of input buttons displayed on the touch display 410.

In operation S1220, the ultrasound diagnosis apparatus 400 may change the display mode of a GUI from a currently displayed mode to another mode, according to the display mode change request of the user. For example, when the current mode is the first display mode, it may be changed to the second display mode, and, when the current mode is the second display mode, it may be changed to the first display mode.

Figure 13:
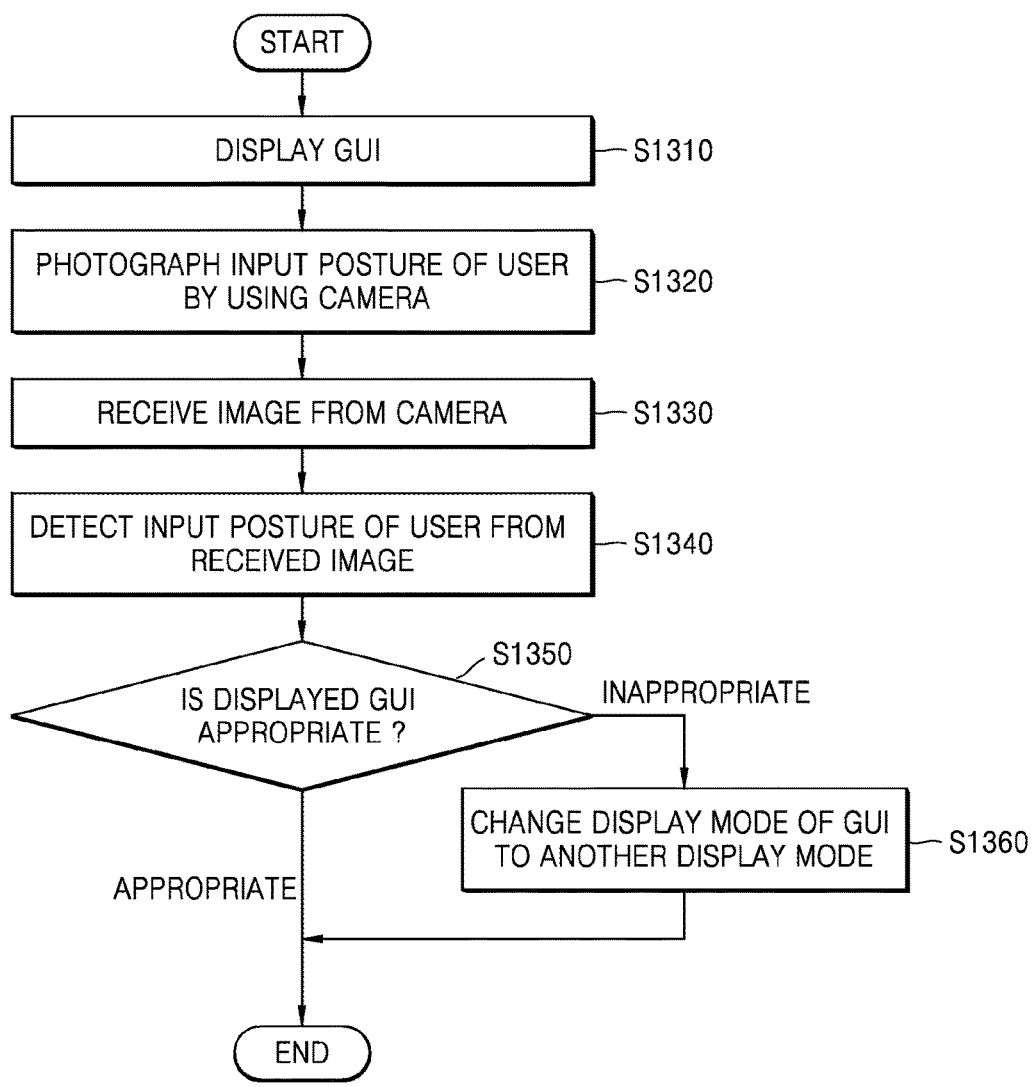
FIG. 13 is a flowchart of a process of changing a display mode according to detection of an input posture of a user via a camera.

FIG. 13 is a flowchart of a process of changing a display mode according to detection of an input posture of a user via a camera.

In operation S1310, the ultrasound diagnosis apparatus 400 may display a GUI including a plurality of input buttons.

In operation S1320, a camera included in or attached to the ultrasound diagnosis apparatus 400 may photograph an input posture of a user.

In operation S1330, the ultrasound diagnosis apparatus 400 may receive an image captured by the camera. The image captured by the camera may be, for example, an image of a user who touches a touch screen.

In operation S1340, the ultrasound diagnosis apparatus 400 may detect the input posture of the user from the received image. A mechanical learning method may be used as a method of detecting an input posture of a user from an image. For example, the ultrasound diagnosis apparatus 400 may be mechanically taught using many images representing previously-distinguished input postures of a user, and thus may detect the input posture of the user when an image captured by the camera is input.

In operation S1350, the ultrasound diagnosis apparatus 400 may compare the detected input posture with a displayed GUI. When the detected input posture of the user is the first input posture and the display mode of the GUI is a second display mode or when the detected input posture of the user is the second input posture and the display mode of the GUI is a first display mode, it may be determined that the displayed GUI is inappropriate. When the displayed GUI is inappropriate, the process may proceed to operation S1360. When the displayed GUI is appropriate, the process of FIG. 13 may be concluded.

In operation S1360, the ultrasound diagnosis apparatus 400 may change the display mode of the GUI to another display mode. For example, when the currently-displayed display mode is the first display mode, the ultrasound diagnosis apparatus 400 may change the currently-displayed display mode to the second display mode, and, when the currently-displayed display mode is the second display mode, the ultrasound diagnosis apparatus 400 may change the currently-displayed display mode to the first display mode.

Figure 14:
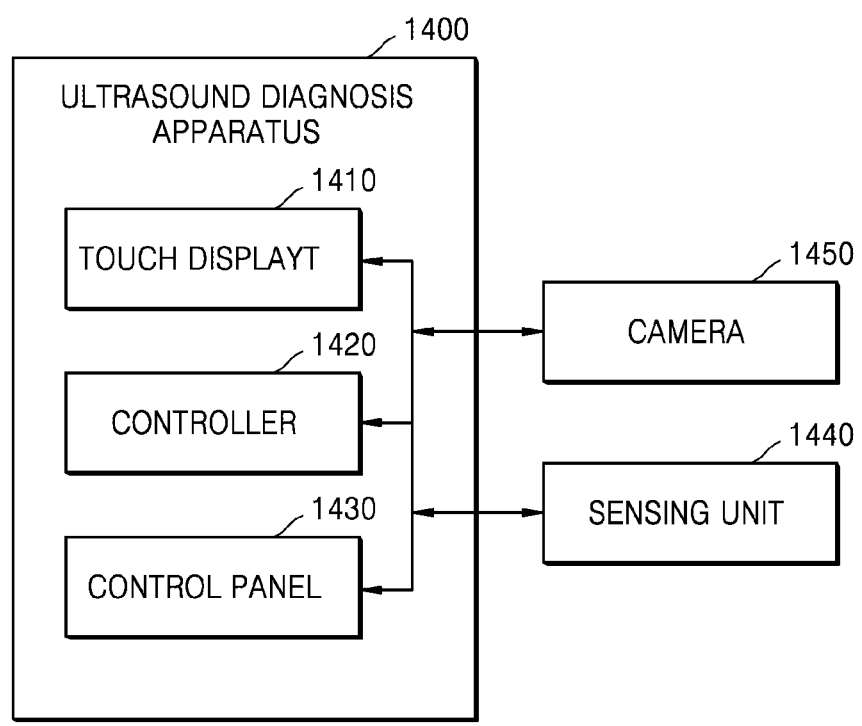
FIG. 14 is a block diagram of an ultrasound diagnosis apparatus including a control panel.

FIG. 14 is a block diagram of an ultrasound diagnosis apparatus 1400 including a control panel 1430.

Referring to FIG. 14, the ultrasound diagnosis apparatus 1400 may include a touch display 1410, a controller 1420, and the control panel 1430. The ultrasound diagnosis apparatus 1400 may further include at least one selected from a sensing unit 1440 for detecting an input posture of a user, and a camera 1450. Although the sensing unit 1440 and the camera 1450 exist outside the ultrasound diagnosis apparatus 1400 in FIG. 14, embodiments of the present invention are not limited thereto, and the sensing unit 1440 and the camera 1450 may exist inside the ultrasound diagnosis apparatus 1400.

The touch display 1410 and the controller 1420 of FIG. 14 may respectively correspond to the touch display 410 and the controller 420 of FIG. 4.

The control panel 1430 may select a measurement mode and a function of the ultrasound diagnosis apparatus 1400 and operate the ultrasound diagnosis apparatus 1400 according to the selected measurement mode and the selected function. The touch display 1410 is detachable from the control panel 1430. The ultrasound diagnosis apparatus 1400 may receive an input for adjusting an ultrasound image from a user, via at least one selected from the touch display 1410 and the control panel 1430.

The sensing unit 1440 may correspond to the sensing unit of FIG. 1, and thus a repeated description thereof will be omitted here.

The camera 1450 may be any type of camera for capturing a 2D or 3D image. For example, the camera 1450 may include a mobile phone, a digital camera, a camcorder, a camera-embedded terminal, or the like.

Figure 15:
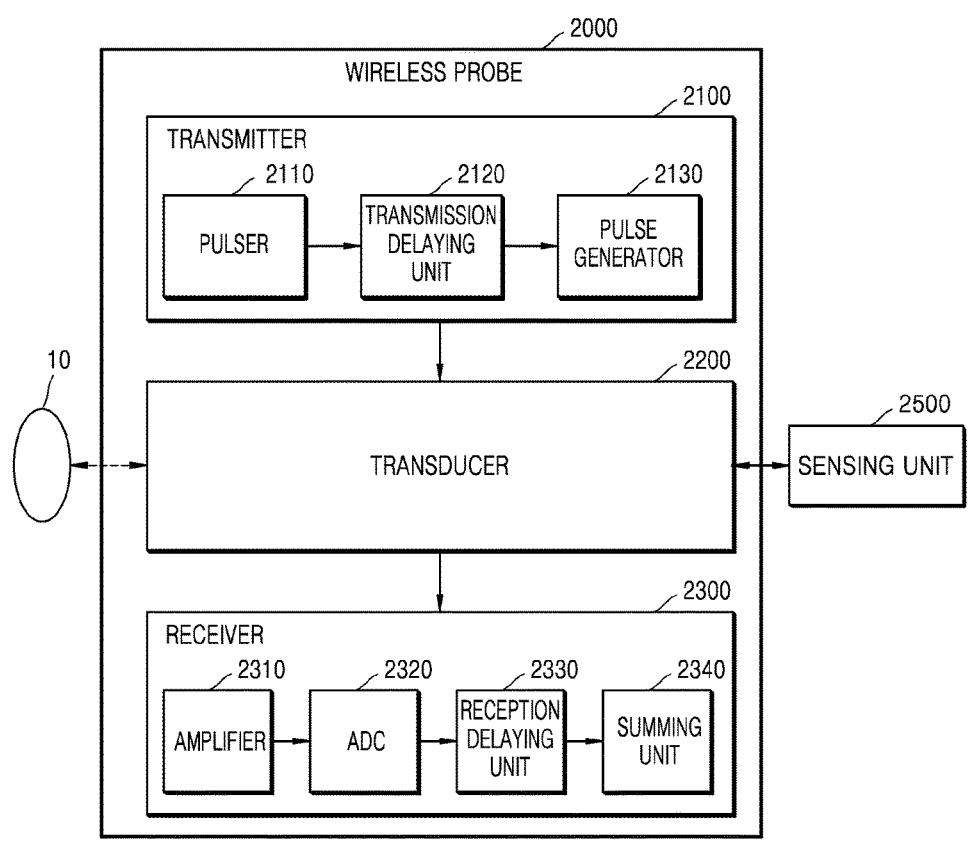
FIG. 15 is a block diagram of a wireless probe according to an embodiment of the present invention.

FIG. 15 is a block diagram of a wireless probe 2000 according to an embodiment of the present invention. As described above with reference to FIG. 3, the wireless probe 2000 may include a plurality of transducers, and, according to embodiments of the present invention, may include some or all of the components of the ultrasound transmission/reception unit 3100 shown in FIG. 3.

The wireless probe 2000 includes a transmitter 2100, a transducer 2200, and a receptor 2300. Since descriptions thereof are given above with reference to FIG. 3, detailed descriptions thereof will be omitted here. Meanwhile, according to embodiments of the present invention, the wireless probe 2000 may selectively include a reception delaying unit 2330 and a summing unit 2340.

The wireless probe 2000 may transmit ultrasound signals to an object 10, receive echo signals from the object 10, generate ultrasound data, and wirelessly transmit the ultrasound data to the ultrasound diagnosis apparatus 3000 of FIG. 3.

A sensing unit 2500 may sense a location, a shape, a gesture, or the like of a hand of a user that grabs the wireless probe 2000. In detail, the sensing unit 2500 may include an RFID sensor, an infrared sensor, an inclination sensor, an ultrasound sensor, a photosensor, or the like. The sensing unit 2500 may acquire information used to determine whether the user manipulates the wireless probe 2000 with the left hand or the right hand, by sensing the location, the shape, the gesture, or the like of the hand of the user. An ultrasound diagnosis apparatus according to an exemplary embodiment of the present invention may detect an input posture of the user, based information corresponding to a result of the sensing of the sensing unit 2500 received from the wireless probe 2000.

The exemplary embodiments should be considered in descriptive sense only and not for purposes of limitation. Descriptions of features or aspects within each embodiment should typically be considered as available for other similar features or aspects in other embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound diagnosis apparatus comprising:
   a touch screen display for configured to display a graphical user interface (GUI) including a plurality of input buttons and receiving an input of a user, wherein the GUI has a first display mode and a second display mode, and the first display mode and the second display mode are modes in which locations of at least one of the plurality of input buttons included in the GUI are differently displayed; and
   a controller configured to detect an input posture of the user based on a relative position of an ultrasound probe with respect to the touch screen display, and setting a display mode of the GUI based on the detected input posture,
   wherein the controller is further configured to detect a user's operation that moves the ultrasound probe horizontally or vertically by a predetermined number of movements or more, and change the display mode of the GUI from one mode to another mode.

2. The ultrasound diagnosis apparatus of claim 1, wherein the at least one of the plurality of input buttons included in the GUI that is displayed in the first display mode is disposed on a side opposite to a side on which the at least one of the plurality of input buttons included in the GUI that is displayed in the second display mode is disposed.

3. The ultrasound diagnosis apparatus of claim 1, wherein the input posture of the user comprises:
   a first input posture in which a left hand of the user manipulates the touch screen display; and
   a second input posture in which a right hand of the user manipulates the touch screen display.

4. The ultrasound diagnosis apparatus of claim 3, wherein the controller sets a display mode of the GUI such that the first display mode and the second display mode respectively correspond to the first input posture and the second input posture.

5. The ultrasound diagnosis apparatus of claim 3, wherein, when the detected input posture of the user is the first input posture and the display mode of the GUI is the second display mode, the controller changes the display mode of the GUI to the first display mode, and, when the detected input posture of the user is the second input posture and the display mode of the GUI is the first display mode, the controller changes the display mode of the GUI to the second display mode.

6. The ultrasound diagnosis apparatus of claim 1, wherein the at least one of the plurality of input buttons comprises at least one selected from a time gain compensation (TGC) button, a Freeze button, a Save button, a B mode button, a Color mode button, a pulse wave (PW) Doppler mode button, and a motion (M) mode.

7. The ultrasound diagnosis apparatus of claim 1, wherein the controller determines the at least one of the plurality of input buttons, based on a user input.

8. The ultrasound diagnosis apparatus of claim 1, wherein the controller detects the number of times each of the plurality of input buttons is used, and determines the at least one of the plurality of input buttons, based on the detected numbers of times.

9. The ultrasound diagnosis apparatus of claim 1, wherein the controller sets the number of the plurality of input buttons included in the GUI, the types of the plurality of input buttons, and the positions of the plurality of input buttons, based on an external input of the user.

10. The ultrasound diagnosis apparatus of claim 1, further comprising a sensor which senses a position of at least one selected from the ultrasound probe and the touch sensor display,
wherein the controller detects the input posture of the user by using the sensor.

11. The ultrasound diagnosis apparatus of claim 10, wherein the sensor comprises at least one selected from a radio frequency identification (RFID) sensor, an infrared sensor, an inclination sensor, an ultrasound sensor, and a photosensor.

12. The ultrasound diagnosis apparatus of claim 1, wherein the controller changes the GUI from one display mode to another display mode, based on a display mode change request of the user.

13. The ultrasound diagnosis apparatus of claim 1, further comprising a camera which photographs the user,
wherein the controller receives an image from the camera and detects the input posture of the user based on the image.

14. A method of controlling an ultrasound diagnosis apparatus, the method comprising:
displaying a GUI including a plurality of input buttons on a touch screen display of the ultrasound diagnosis apparatus, wherein the GUI has a first display mode and a second display mode, and the first display mode and the second display mode are modes in which locations of at least one of the plurality of input buttons included in the GUI are differently displayed;
detecting an input posture of a user based on a relative position of an ultrasound probe of the ultrasound diagnosis apparatus with respect to the touch screen display; and
setting a display mode of the GUI based on the detected input posture,
wherein the setting of the display mode of the GUI comprises detecting a user's operation that moves the ultrasound probe horizontally or vertically by a predetermined number of movements or more, and changing the display mode of the GUI from one mode to another mode.

15. The method of claim 14, wherein the plurality of input buttons included in the GUI that is displayed in the first display mode are disposed on a side opposite to a side on which the plurality of input buttons included in the GUI that is displayed in the second display mode are disposed.

16. The method of claim 14, wherein the input posture of the user comprises:
a first input posture in which a left hand of the user manipulates the plurality of input buttons; and
a second input posture in which a right hand of the user manipulates the plurality of input buttons.

17. The method of claim 16, wherein the setting of the display mode of the GUI comprises setting a display mode of the GUI such that the first display mode and the second display mode respectively correspond to the first input posture and the second input posture.

18. The method of claim 16, wherein the setting of the display mode of the GUI comprises:
when the detected input posture of the user is the first input posture and the display mode of the GUI is the second display mode, changing the display mode of the GUI to the first display mode; and
when the detected input posture of the user is the second input posture and the display mode of the GUI is the first display mode, changing the display mode of the GUI to the second display mode.

19. The method of claim 14, wherein the at least one of the plurality of input buttons comprises at least one selected from a TGC button, a Freeze button, a Save button, a B mode button, a Color mode button, a PW Doppler mode button, and a M mode.

20. The method of claim 14, wherein the setting of the display mode of the GUI comprises determining the at least one of the plurality of input buttons, based on a user input.

21. The method of claim 14, wherein the setting of the display mode of the GUI comprises:
detecting the number of times each of the plurality of input buttons is used; and
determining the at least one of the plurality of input buttons, based on the detected numbers of times.

22. The method of claim 14, wherein the setting of the display mode of the GUI further comprises changing at least one selected from the number of the plurality of input buttons included in the GUI, the types of the plurality of input buttons, and the positions of the plurality of input buttons, based on an external input of the user.

23. The method of claim 14, further comprising sensing a position of at least one selected from the ultrasound probe and the touch screen display,
wherein the setting of the display mode of the GUI comprises detecting the input posture of the user, based on the sensed position of the at least one selected from the ultrasound probe and the touch screen display.

24. The method of claim 23, wherein the sensing of the position of the at least one selected from the ultrasound probe and the touch screen display comprises sensing the position of the at least one selected from the ultrasound probe and the touch screen display, by using at least one selected from a radio frequency identification (RFID) sensor, an infrared sensor, an inclination sensor, an ultrasound sensor, and a photosensor.

25. The method of claim 14, wherein the setting of the display mode of the GUI further comprises changing the GUI from one display mode to another display mode, based on a display mode change request of the user.

26. The method of claim 14, further comprising photographing the user by using a camera,
wherein the setting of the display mode of the GUI comprises:
receiving an image from the camera; and
detecting the input posture of the user, based on the image.

27. A non-transitory computer-readable recording medium having recorded thereon a program, that when executed by a processor, performs the steps of:

displaying a GUI including a plurality of input buttons on a touch screen display of the ultrasound diagnosis apparatus, wherein the GUI has a first display mode and a second display mode, and the first display mode and the second display mode are modes in which locations of at least one of the plurality of input buttons included in the GUI are differently displayed;

detecting an input posture of a user based on a relative position of an ultrasound probe of the ultrasound diagnosis apparatus with respect to the touch screen display;

setting a display mode of the GUI based on the detected input posture; and wherein the setting of the display mode of the GUI comprises detecting a user's operation that moves the ultrasound probe horizontally or vertically by a predetermined number of movements or more, and changing the display mode of the GUI from one mode to another mode.

28. An ultrasound diagnosis apparatus comprising:

a control panel configured to select a measurement mode and a function of the ultrasound diagnosis apparatus and operates the ultrasound diagnosis apparatus according to the selected measurement mode and the selected function;

a touch screen display which is detachable from the control panel, configured to display a graphical user interface (GUI) including a plurality of input buttons, and receive an input of a user, wherein the GUI has a first display mode and a second display mode, and the first display mode and the second display mode are modes in which locations of at least one of the plurality of input buttons included in the GUI are differently displayed; and a controller configured to detect an input posture of the user based on a relative position of an ultrasound probe with respect to the control panel and set a display mode of the GUI based on the detected input posture, wherein the controller is further configured to detect a user's operation that moves the ultrasound probe horizontally or vertically by a predetermined number of movements or more, and change the display mode of the GUI from one mode to another mode.

* * * * *